United States Patent [19]
Graves

[11] Patent Number: 5,271,391
[45] Date of Patent: Dec. 21, 1993

[54] APPARATUS FOR DELIVERING A CONTINUOUS POSITIVE AIRWAY PRESSURE TO AN INFANT

[76] Inventor: Linda Graves, 3658 Grantley, Toledo, Ohio 43613

[21] Appl. No.: 811,013

[22] Filed: Dec. 20, 1991

[51] Int. Cl.$^5$ ............................................. A61M 16/00
[52] U.S. Cl. ............................ 128/207.18; 128/207.13
[58] Field of Search ................. 128/207.18, 204.18, 128/205.13, 205.25, 206.21, 207.13, 200.24, 730

[56] References Cited

U.S. PATENT DOCUMENTS

| | | | |
|---|---|---|---|
| 4,156,426 | 5/1979 | Gold | 128/204.18 |
| 4,249,527 | 2/1981 | Ko | 128/204.18 |
| 4,278,082 | 7/1981 | Blackmer | 128/207.18 |
| 4,774,946 | 10/1988 | Ackerman | 128/207.18 |
| 4,821,709 | 4/1989 | Jensen | 128/204.21 |
| 5,040,532 | 8/1991 | Alfery | 128/207.15 |
| 5,117,819 | 6/1992 | Servidio | 128/204.18 |

FOREIGN PATENT DOCUMENTS

| | | | |
|---|---|---|---|
| 146688 | 2/1981 | German Democratic Rep. | 128/207.18 |
| 155585 | 6/1982 | German Democratic Rep. | 128/207.18 |
| 618570 | 5/1949 | United Kingdom | |

OTHER PUBLICATIONS

Kaufmann, "The Universe", Freeman & Co., NY, 1985, p. 157.

*Primary Examiner*—David A. Wiecking
*Assistant Examiner*—Eric P. Raciti
*Attorney, Agent, or Firm*—Marshall & Melhorn

[57] ABSTRACT

A method of and apparatus for delivering a continuous positive airway pressure to an infant by the use of a light-weight, flexible nasal cannula. The nasal cannula is connected to a source of positive air flow by a pair of flexible hoses. The soft nasal outlets of the cannula reduce damage to the nasal passages of an infant when the outlets are being inserted. The pliable body of the cannula is formed to occlude the nasal passages and prevent leakage. The flexible hoses are gently secured to the cheeks of the infant. The infant can rest in a variety of positions and the medical staff has easy access to the infant.

4 Claims, 1 Drawing Sheet

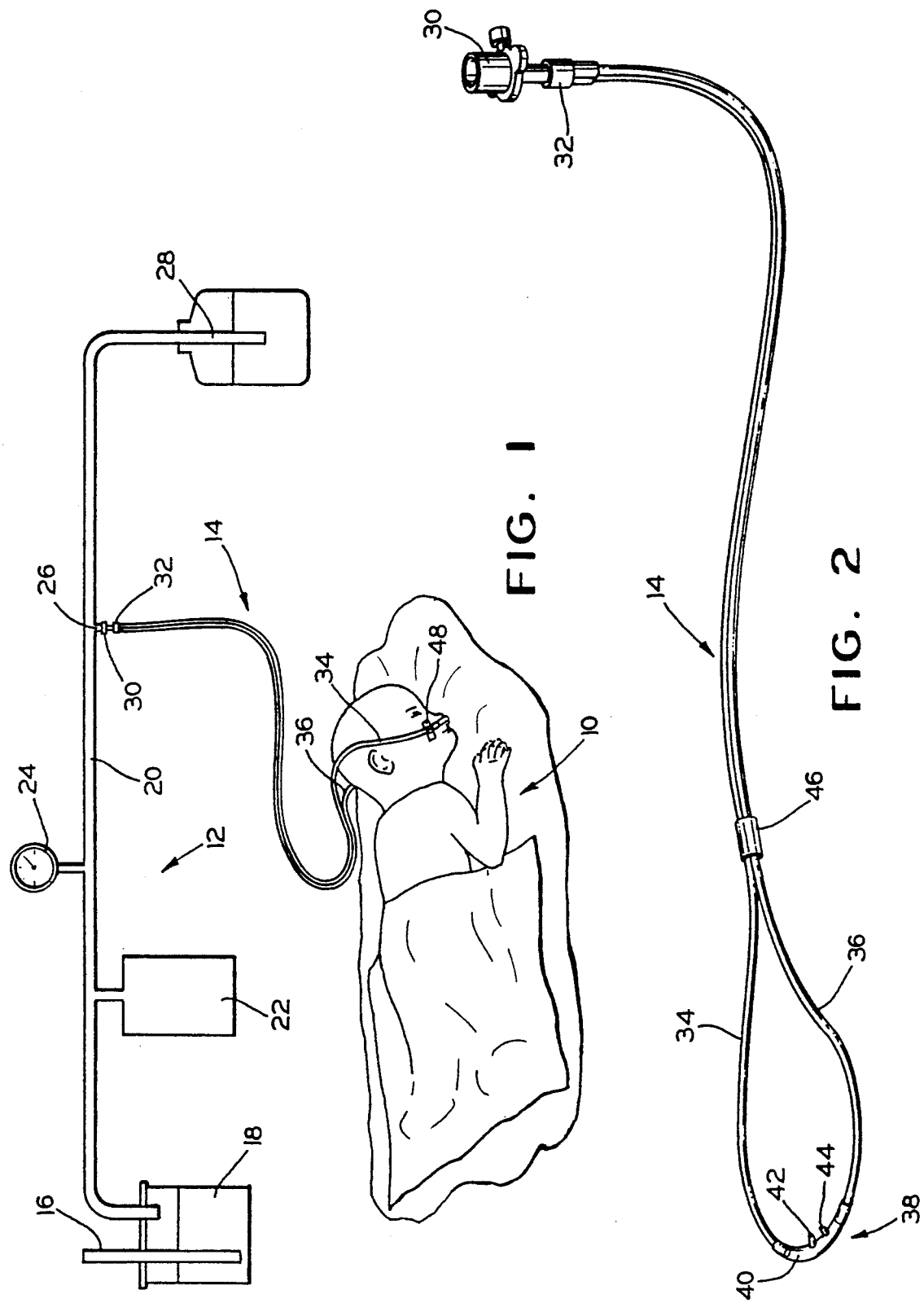

APPARATUS FOR DELIVERING A CONTINUOUS POSITIVE AIRWAY PRESSURE TO AN INFANT

BACKGROUND OF THE INVENTION

This invention relates generally to delivering a continuous positive air pressure, and more particularly to an improved apparatus for delivering a continuous positive air pressure to an infant.

The medical profession has used positive pressure therapy to treat ventilatory insufficiency since 1936. Continuous distending pressure ("CDP") is the maintenance of an increase transpulmonary pressure during the expiratory phase of respiration. CDP is a general term used to denote continuous positive airway pressure ("CPAP") when the patient is breathing spontaneously or positive end-expiratory pressure ("PEEP") when the patient is assisted on ventilation. CDP systems were initially used primarily for adult respiratory problems. By 1971, medical reports documented the use of CPAP in spontaneously breathing newborn infants with idiopathic respiratory distress syndrome.

The benefits of an increased alveolar pressure for use on infants with respiratory distress syndrome have been recognized for a number of years. The use of CPAP has also been extended into the treatment of neonatal problems other than respiratory distress syndrome, such as apnea of prematurity, patent ductus arteriosus, meconium aspiration syndrome and post-surgical cases. Several methods of delivering CPAP from a positive air flow source to infants have been used, including endotracheal tube, head box, face chamber, face mask, and nasal/nasopharyngeal prongs.

CPAP keeps lungs expanded on exhalation while an infant does its own breathing. CPAP keeps the lungs from collapsing on exhalation and allows a more efficient exchange of oxygen and carbon dioxide to occur. CPAP reduces the effort required to breathe and breathing is typically more regular with infants on a CPAP system.

Many devices and systems are currently available to provide a CPAP source. These devices and systems function on substantially the same principle and typically employ a continuous gas flow, a reservoir bag, a valve to produce above ambient expiratory pressure, and a humidification device. The amount of CPAP may be varied by changing the amount of gas flowing into the system or by changing the amount of obstruction to outflow. Gas flow is regulated through a flow meter. Flow through the circuit is a function of the resistance to flow determined by the diameter and length of the associated tubing.

The endotracheal tube was the original system used to deliver CPAP in infants. The endotracheal tube allows the use of low flows while maintaining high pressure with minimum leakage. However, the endotracheal tube causes acute airway trauma. The endotracheal tube can becomes kinked or blocked during or following insertion. Tracheal stenosis, scaring and severe irritation are possible by the use of such system.

The head chamber is a non-invasive, closed system that permits the use of low flows. The head chamber is not effective for small infants weighing less than 1,500 grams. With the head chamber, there is a delay in access to the face and mouth. The infant is inaccessible and movement is limited. This modality produces high noise levels and has been associated with certain neck problems for infants using the head chamber.

The face chamber has similar problems to the head chamber. During application, the patient must be in a cradle for positioning purposes. The face chamber has not gained wide acceptance in the United States.

The face mask is a simple and inexpensive option for delivering CPAP to an infant. The mask must be securely placed and must cover both nose and mouth. Pressure buildup and carbon dioxide retention are possible problems which may occur with use of the face mask for CPAP. The face mask may produce severe gastric distension and typically requires an orogastric for decompression.

Nasal prongs and nasopharyngeal prongs are another system for applying CPAP. Nasal prongs are easy to apply and avoid the complication of endotracheal intubation. The current nasal prong designs are rigid structures which may cause trauma to the infant's nasal septum and turbinotes. When used with infants, crying is usually excessive and the infant loses pressure and inhales room air. The current nasal prongs are bulky and typically must be secured in a fixed position above the infant's head. The infant is required to lie on its back when connected to the system to assure proper operation of the nasal prongs.

Although there are may benefits to CPAP, there are some possible adverse affects, such as harmful effects on cardiac output and intracranial pressure. Such effects may be avoided by careful monitoring of distending pressure. Pulmonary air leaks and over distention of the lungs are also potential complications. Nasal CPAP is one of the least dangerous methods for applying CPAP. However, doctors and other hospital staff employees have found the present methods of applying CPAP either difficult to work with or highly uncomfortable for infants. Hospitals have a need for a new method of delivering CPAP to infants with respiratory problems.

SUMMARY OF THE INVENTION

In accordance with the present invention, there is provided an improved method of and apparatus for delivering a continuous positive airway pressure to an infant by the use of a light-weight flexible nasal cannula. A source of positive air flow is placed near the infant and a pair of flexible hoses extend from the source of positive air flow to the nasal cannula. After the hoses are affixed to the appropriate cannula openings, the flexible outlets of the cannula are placed in the nose of the infant. The hose arrangement is adjustable for infant comfort and medical staff convenience. The cannula can be anchored to the face of the infant via one or two pieces of pressure sensitive adhesive tape.

An object of the present invention is to permit the infant to rest in a variety of positions. The infant can lie on its stomach without affecting the operation of the CPAP delivery system. The current invention does not restrict the head or movement of the infant. Doctors and other medical staff have easy access to the mouth, face, and scalp of the infant. It is also much easier to maneuver and examine the infant during feeding and treatment.

The method of and apparatus for CPAP delivery to infants in the present invention is more convenient to set up and use than the other methods of CPAP delivery, but has no additional disadvantages when compared to the current systems. The soft nasal outlets do little or no damage to the nasal passages of the infant. Existing sources of air flow can be used with the current invention, so new sources of positive air flow are not required.

The cannula is pliable to provide a good fit for sealing the nasal passages and preventing leaks of the positive air flow. The soft cannula fit of the present invention provides a better seal than the hard cannula fit of other nasal prong systems. Other nasal prong systems use long, rigid outlets to extend into the nasal passages, which reduces leakage but increases the irritation to the nasal passages. In contrast, the outlets of the present invention can be significantly shorter than the outlets of other nasal prong systems. The shorter, pliable outlets cause less trauma to the nasal passages of the infant.

Another object of the present invention is to facilitate the touching and holding of the infant while the infant is still connected to the system. If longer flexible hoses are used, the infant can be moved about and held without interrupting the CPAP therapy. This ability to maneuver and hold the infant is important to the comfort of the infant and also allows the medical staff and parents of the infant to develop the bonds of touch and feel with the infant.

Because the delivery system of the present invention causes less trauma and provides additional comfort over existing systems, infants tend to cry less and have more regular breathing patterns when using the present invention.

BRIEF DESCRIPTION OF THE DRAWINGS

The above, as well as other advantages of the present invention, will become readily apparent to those skilled in the art from the following detailed description of a preferred embodiment when considered in the light of the accompanying drawings in which:

FIG. 1 is a schematic view of a system embodying the continuous positive airway pressure system of the present invention; and FIG. 2 is an enlarged perspective view of the nasal cannula, flexible hoses, and adapter illustrated in FIG. 1 to deliver a continuous positive airway pressure from a source to an infant.

DESCRIPTION OF THE PREFERRED EMBODIMENT

Referring now to the drawings, there is illustrated in FIGS. 1 and 2, the continuous positive airway pressure delivery method and apparatus of the present invention. An infant 10 has been connected to a positive air flow source 12 by a nasal cannula system 14. Gas enters the positive air flow source 12 through an intake tube 16. After passing through the humidifier 18, the gas is delivered through a delivery tube 20 to a reservoir bag 22. The reservoir bag 22 has a check valve which opens during spontaneous inspiration and closes during exhalation. Pressure in the system is monitored by a pressure gauge 24. The gas continues through the tube 20 to a T-shaped fitting 26. Continuous positive airway pressure is maintained in the system by using an underwater tube 28.

The nasal cannula system 14 is connected to the fitting 26 by a ventilation adapter 30. Gas from the tube 20 flows through the adapter 30, through a fitting 32, and communicate with flexible hoses 34 and 36 which are adapted to deliver the gas to the cannula 38. The main body 40 of cannula 38 has two nasal outlets 42 and 44 extending perpendicularly from the outer wall of the main body 40. The nasal outlets 42 and 44 are designed for insertion into the nose of infant 10. The gas is delivered from the cannula 38 through the nasal outlets 42 and 44.

The cannula 38 and nasal outlets 42 and 44 are made of a light-weight, flexible polyvinyl material to minimize any damages to the nasal passages in the infant 10 when inserting and withdrawing the nasal outlets 42 and 44. Because the nasal cannula 38 is so light, the nasal cannula 38 can typically be held in place by affixing hoses 34 and 36 to the cheeks of the infant 10 by a pressure sensitive adhesive tape 48.

The cannula body 40 is very pliable which minimizes the pressure contact injuries to the infant 10. Leakage in the CPAP system at the point of delivery to the infant can decrease the effectiveness of the system. The outlets 42 and 44 of the present invention are very short and pliable to easily conform to the shape of the infant's nasal passages. In addition, leakage problems are minimized in the present invention because the pliable cannula body 40 can be formed and taped in position to effectively seal the nasal passages without injury or discomfort to the infant 10.

The flexible hoses 34 and 36 permit the infant to be freely maneuvered in relation to the positive air flow source 12. If additional maneuverability is required, the lengths of the hoses 34 and 36 can be extended. The hoses 34 and 36 are of sufficient rigidity so that the air flow will not be diminished in the hoses, even if the infant is lying directly on one or both of the hoses.

A slidable clasp 46 is used to secure the two hoses 34 and 36 around the head of the infant 10. The two hoses 34 and 36 are adjacent to each other when leaving the fitting 32 and are separated on opposite sides of the cannula body 40. The two hoses 34 and 36 are separated wide enough to fit over the head of an infant 10. The slidable clasp 46 can be adjusted so that the two hoses 34 and 36 are comfortably positioned around the head of an infant 10. This method of providing CPAP allows the infant 10 to rest on its side or its stomach, while still maintaining the CPAP.

In addition to the benefits of improved maneuverability, the medical staff is provided with easy access to the mouth and face of the infant 10. The comfort of the infant 10 is increased since the infant 10 can be placed on its stomach or side without effecting the delivery of the air source. Typically, very little trauma is suffered in the nasal passages or cheeks of the infant 10.

The continuous positive airway pressure delivery method of the present invention is designed primarily for infants ranging from 500 grams to 4500 grams in weight. The source of positive air flow can be maintained at similar settings used with other delivery methods. The pulse oximeter is maintained at a rating of 91-94 with a 21% to 100% oxygen content and a flow rate of 4-8 liters per minute. The pressure of the CPAP is maintained between 2-12 cm of $H_2O$. Pressure is a crucial aspect of the therapy and such pressure can be carefully monitored on the pressure gauge 24.

In accordance with the provisions of the patent statutes, the present invention has been described in what is considered to represent its preferred embodiment. However, it should be noted that the invention can be practiced otherwise than as specifically illustrated and described without departing from its spirit and scope.

What is claimed is:

1. An apparatus for delivering a continuous positive airway pressure to the nasal passages of an infant weighing between 500 grams and 4500 grams, comprising:

a) a cannula having a deformable body for sealably engaging a nose of an infant, said cannula including two short, deformable outlets extending outwardly from the deformable body in parallel spaced-apart relationship;

b) means for providing communication between the deformable body of said cannula and a source of positive air flow; and c) means for securing said cannula to an infant, whereby the deformable outlets of said cannula are inserted into the nasal passages with only incidental contact between the outlets and the nasal passages, said securing means for positioning the deformable body of said cannula to both occlude the nasal passages and deliver a positive airway pressure through the outlets to the nasal passages of an infant.

2. An apparatus for delivering a continuous positive airway pressure to the nasal passages of an infant weighing between 500 grams and 4500 grams, comprising:

a) a cannula having a deformable body for sealably engaging a nose of an infant, said cannula including two short, deformable nasal outlets extending outwardly from the deformable body in parallel spaced-apart relationship;

b) two flexible air hoses connected to the deformable body of said cannula in the region of the head of the infant and extending to a source of positive air flow;

c) a fitting for facilitating fluid communication between said hoses and the source of positive air flow; securing means for positioning the deformable body of said cannula to both occlude the nasal passages and deliver a positive airway pressure through the outlets to the nasal passages of an infant, said securing means further comprising a slidable clasp and a piece of tape d) said slidable clasp encircling said air hoses for positioning and securing the air hoses about the head of the infant; and e) said piece of tape attached to one of the hoses for securing the hose and said cannula to the infant whereby the deformable outlets are inserted into the nasal passages with only incidental contact between the outlets and the nasal passages.

3. The apparatus defined in claim 1 wherein said means to provide communication includes a pair of flexible air hoses connected to the body of said cannula in a spaced apart relationship about the head of the infant and extending from said cannula to a fitting on the source of positive air flow.

4. The apparatus defined in claim 3 wherein said means for variably securing said cannula includes a slidable clamp encircling said pair of flexible hoses whereby the space between said pair of flexible hoses is adjusted by sliding the clasp towards the cannula to secure said hoses around the head of the infant.

* * * * *